(12) United States Patent
Chandler, Jr.

(10) Patent No.: US 9,439,799 B2
(45) Date of Patent: Sep. 13, 2016

(54) JOINT SUPPORT DEVICE

(71) Applicant: Franklin Woodrow Chandler, Jr., Northport, AL (US)

(72) Inventor: Franklin Woodrow Chandler, Jr., Northport, AL (US)

(*) Notice: Subject to any disclaimer, the term of this patent is extended or adjusted under 35 U.S.C. 154(b) by 322 days.

(21) Appl. No.: 14/046,422

(22) Filed: Oct. 4, 2013

(65) Prior Publication Data

US 2014/0100502 A1    Apr. 10, 2014

Related U.S. Application Data

(60) Provisional application No. 61/709,744, filed on Oct. 4, 2012.

(51) Int. Cl.
*A61F 5/01* (2006.01)
*D04H 3/05* (2006.01)

(52) U.S. Cl.
CPC .......... *A61F 5/0123* (2013.01); *A61F 5/0109* (2013.01); *D04H 3/05* (2013.01)

(58) Field of Classification Search
CPC ............ D04C 1/06; D04H 3/05; D04H 3/07; A61F 5/0123; A61F 5/0109
See application file for complete search history.

(56) References Cited

U.S. PATENT DOCUMENTS

| | | | | |
|---|---|---|---|---|
| 2,456,507 A * | 12/1948 | Hendrickson | ......... | A61F 15/005 602/63 |
| 2,844,146 A * | 7/1958 | Perdue | .................. | A61F 15/005 29/235 |
| 3,097,644 A * | 7/1963 | Parker | ............... | A61F 13/00072 206/440 |
| 3,263,682 A * | 8/1966 | Rosenfield | ............ | A61F 13/105 2/21 |
| 3,934,583 A | 1/1976 | Hollingshead | | |
| 3,945,046 A | 3/1976 | Stromgren | | |
| 4,926,851 A * | 5/1990 | Bulley | .................. | A61F 13/105 128/856 |
| 5,499,966 A * | 3/1996 | Bulley | ................ | A61F 5/05875 602/41 |
| 5,512,039 A | 4/1996 | White | | |
| 6,412,386 B1 * | 7/2002 | Tseng | ....................... | D04C 1/12 87/9 |
| 2006/0164826 A1 * | 7/2006 | Ackermann | ......... | A44B 15/005 362/157 |
| 2007/0073205 A1 * | 3/2007 | Hull | .................... | A61F 5/05875 602/22 |
| 2012/0271403 A1 * | 10/2012 | Gries | ....................... | D04C 1/06 623/1.15 |

* cited by examiner

*Primary Examiner* — Shaun R Hurley
(74) *Attorney, Agent, or Firm* — Dunlap Bennett & Ludwig PLLC

(57) ABSTRACT

A joint support device is provided. The joint support device may include a first tubular layer and a second tubular layer both made of crisscrossing fibers. The crisscrossing fibers of the first tubular layer may be oriented in a spiral in a first direction and the crisscrossing fibers of the second tubular layer may be oriented in a spiral in an opposite direction of the first direction. The first and second tubular layers may be layered together and may be attached to an existing elastic knee brace.

3 Claims, 4 Drawing Sheets

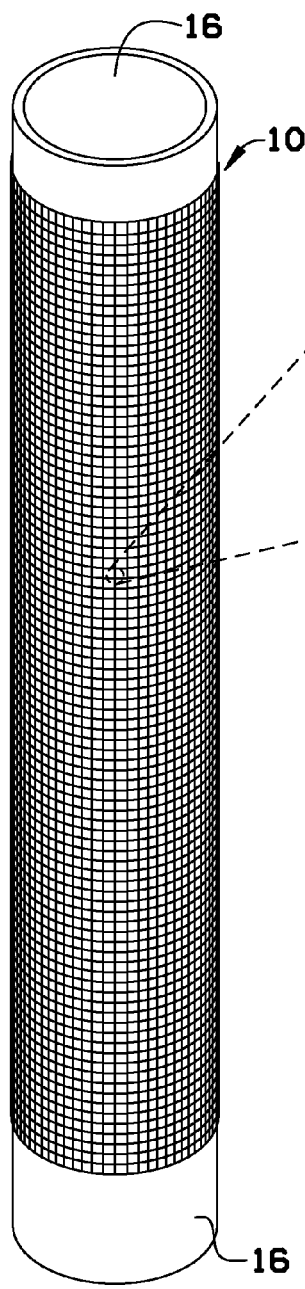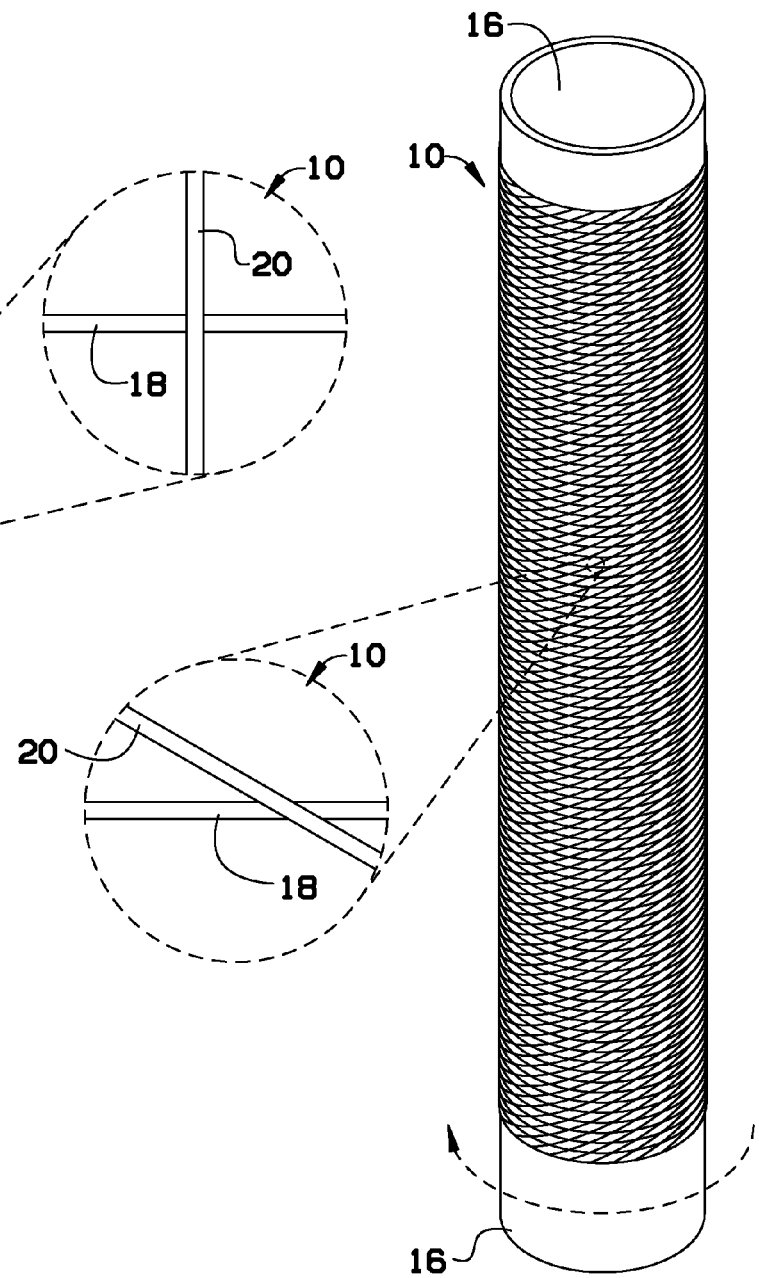
FIG. 3
FIG. 4

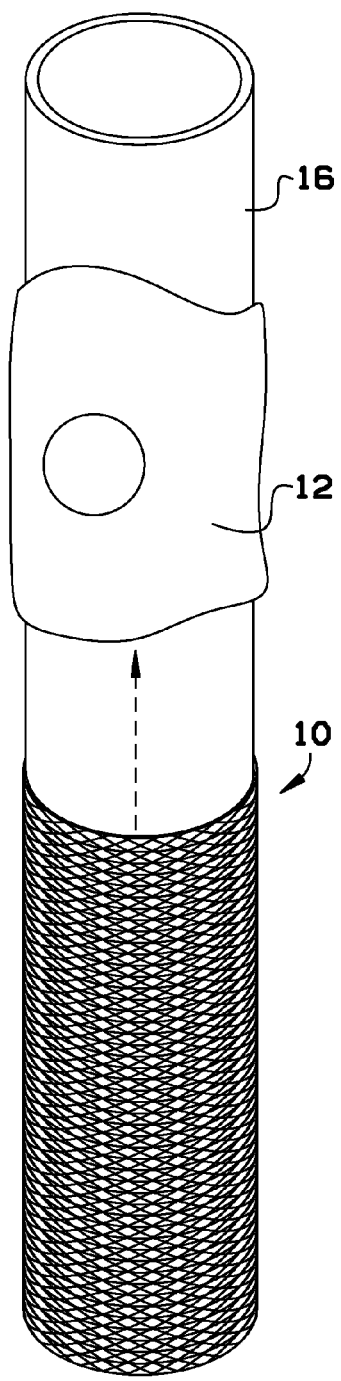
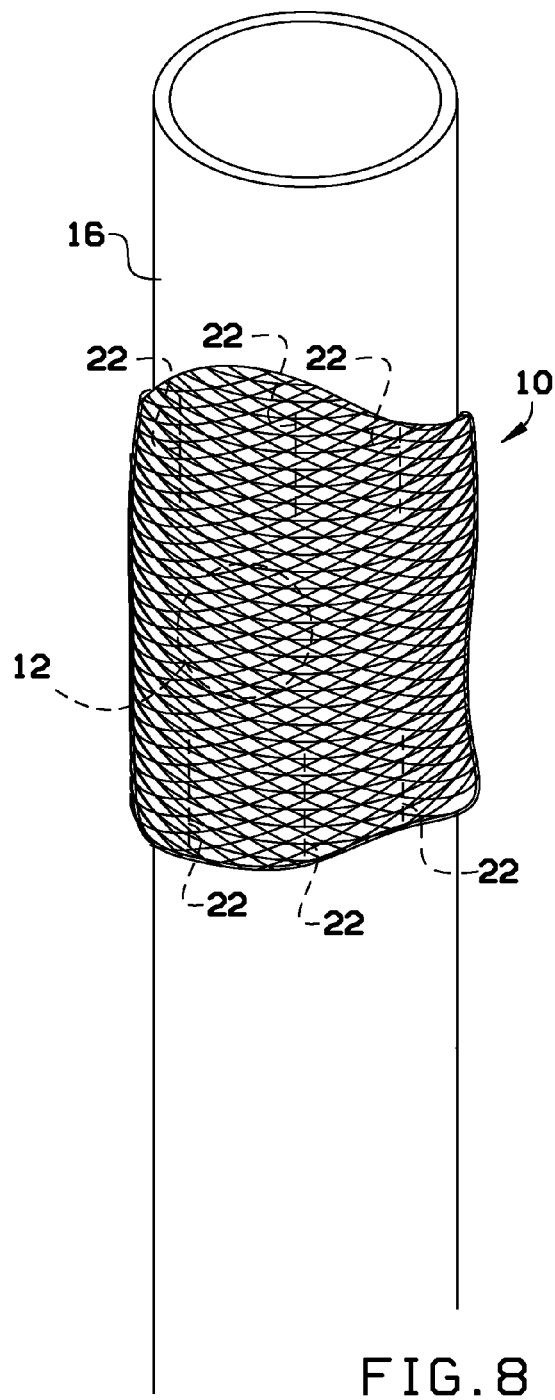
FIG.7
FIG.8

JOINT SUPPORT DEVICE

CROSS-REFERENCE TO RELATED APPLICATION

This application claims the benefit of priority of U.S. provisional application No. 61/709,744, filed Oct. 4, 2012, the contents of which are herein incorporated by reference.

BACKGROUND OF THE INVENTION

The present invention relates to a joint support device and, more particularly, to a joint support device that may attach to an elastic knee brace.

A knee orthosis (KO) or knee brace is a brace that extends above and below the knee joint and is generally worn to support or align the knee. In the case of diseases causing neurological or muscular impairment of muscles surrounding the knee, a KO can prevent flexion or extension instability of the knee. In the case of conditions affecting the ligaments or cartilage of the knee, a KO can provide stabilization to the knee by replacing the function of these injured or damaged parts. For instance, knee braces can be used to relieve pressure from the part of the knee joint affected by diseases such as arthritis or osteoarthritis by realigning the knee joint into valgus or varus. In this way a KO may help reduce osteoarthritis pain.

Existing elastic knee braces work as compressive devices providing minimal support. The elastic braces allow the knees to twist and rotate. The twisting and rotation of the wearer's knee causes a majority of knee injury in athletics. Steel or other action limiting knee braces limit athletic performance to a degree so that the braces cannot be used comfortably during sports. Further, the present day elastic knee braces are ineffective and therefore are generally not used as well.

As can be seen, there is a need for an improved knee brace device that allows movement while still preventing injury.

SUMMARY OF THE INVENTION

In one aspect of the present invention, a joint support device comprises: a first tubular layer having a top and a bottom, wherein the first tubular layer comprises a plurality of first crisscrossing fibers, wherein the first crisscrossing fibers spiral from the bottom to the top; a second tubular layer having a top and a bottom, wherein the second tubular layer comprises a plurality of second crisscrossing fibers, wherein the second crisscrossing fibers spirals from the bottom to the top in an opposite direction of the first crisscrossing fibers, wherein the first tubular layer and the second tubular layer overlap one another.

In another aspect of the present invention, a method of making a joint support device comprises: suspending a first tubular layer on a cylinder, wherein the first tubular layer comprises a top and a bottom and crisscrossing fibers; twisting the first tubular layer in a first direction to create a first spiral; suspending a second tubular layer on a cylinder, wherein the second tubular layer comprises a top and a bottom and crisscrossing fibers; twisting the second tubular layer in an opposite direction relative to the first direction to create a second spiral; and layering the first tubular layer with the second tubular layer.

These and other features, aspects and advantages of the present invention will become better understood with reference to the following drawings, description and claims.

BRIEF DESCRIPTION OF THE DRAWINGS

FIG. 3 is a perspective view of the present invention shown in development stage and demonstrated in a non-twisted state;

FIG. 4 is a perspective view of the present invention shown in development stage and demonstrated in a twisted state;

FIG. 7 is an exploded view of the present invention shown in application over an exemplary knee brace; and FIG. 8 is a perspective view of the present invention attached to the exemplary knee brace of FIG. 7.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a joint support device. The joint support device may include a first tubular layer and a second tubular layer both made of crisscrossing fibers. The crisscrossing fibers of the first tubular layer may be oriented in a spiral in a first direction and the crisscrossing fibers of the second tubular layer may be oriented in a spiral in an opposite direction of the first direction. The first and second tubular layers may be layered together and may be attached to an existing elastic knee brace.

The present invention may include a joint support device such as a knee support. The knee support of the present invention may limit the rotation of the upper leg in relation to the lower leg, and may thereby prevent injury. The present invention may have a tubular shape, with an elastic fabric in one direction and inelastic in another direction. The present invention may include two layers of fabric that are rotated in opposite directions from the top to the bottom. The present invention may attach to any existing elastic knee brace to prevent rotation of the knee, and thereby allow existing elastic knee braces to function at a higher level and prevent knee injuries. The present invention may hold bendable side stays in many existing knee braces to remain in place and function to limit side buckling of individual's knee.

Figures 1, 2:
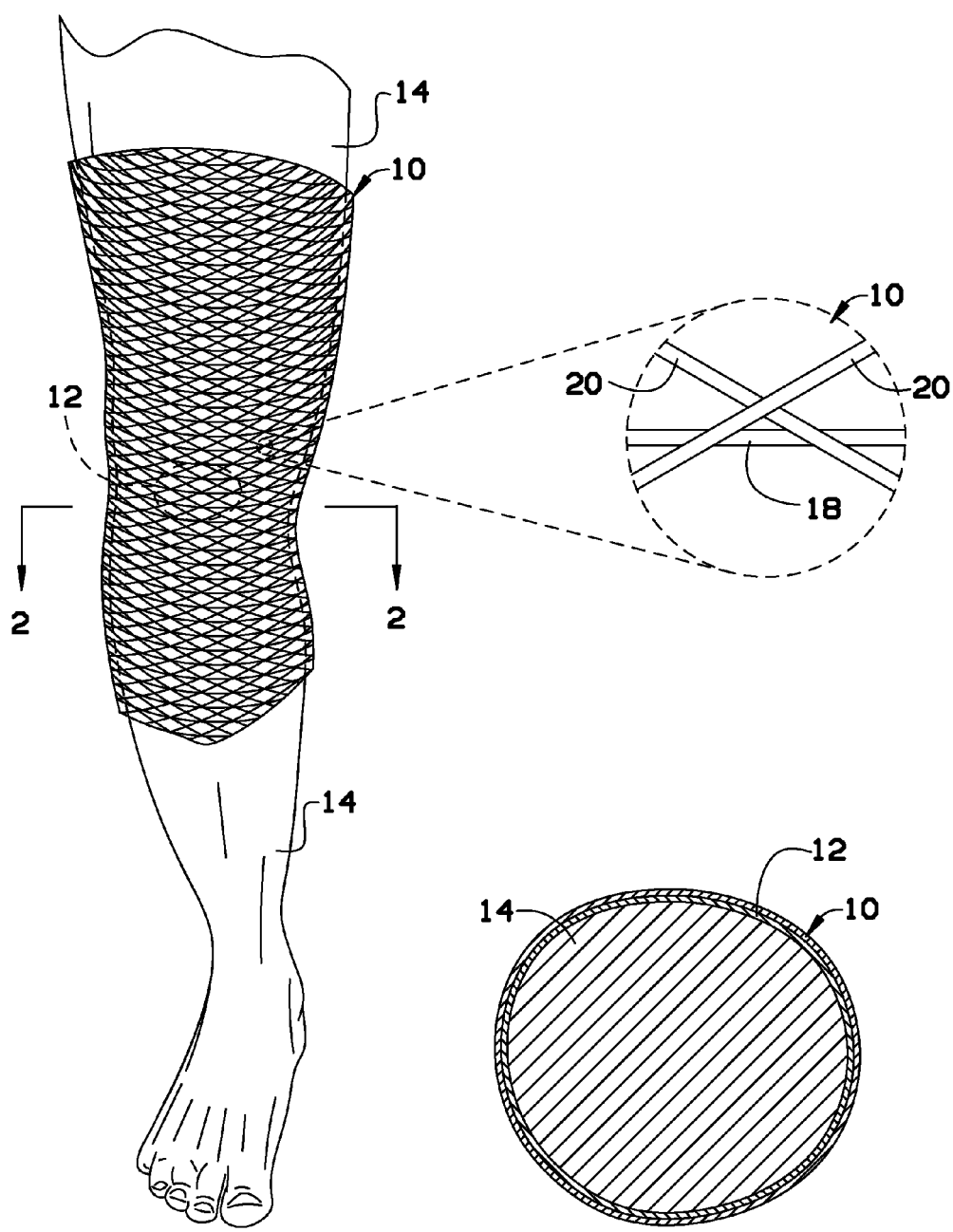
FIG. 1 is a perspective view of the present invention shown in use.
FIG. 2 is a section view of the present invention along line 2-2 in FIG. 1.
Figure 5:
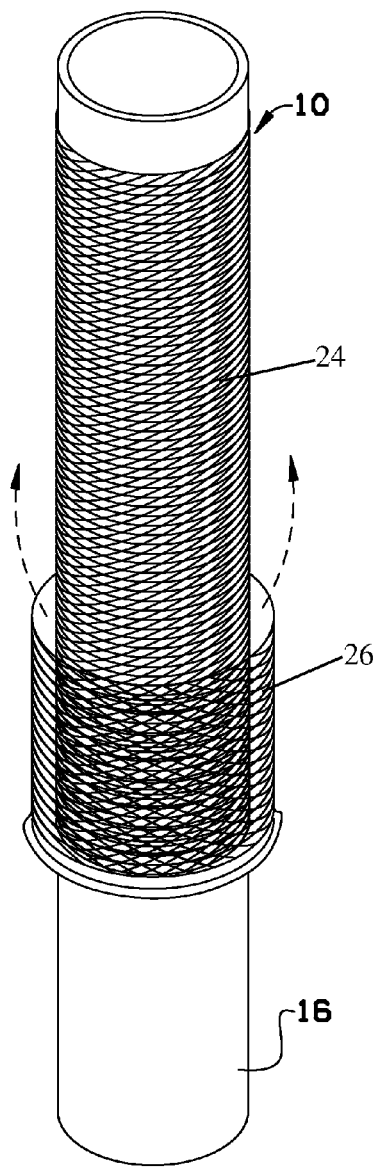
FIG. 5 is a perspective view of the present invention shown in development stage demonstrating the layering of the tubular layers.
Figure 6:
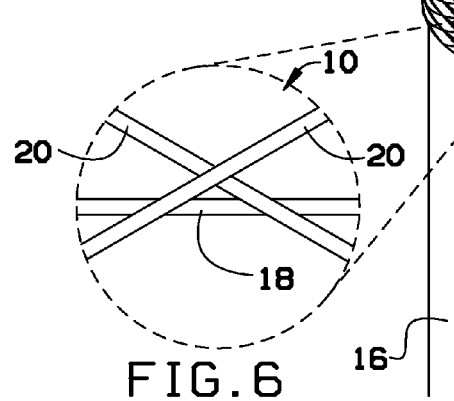
FIG. 6 is a perspective view of the present invention shown in development stage demonstrating the completed layering of the tubular layers.

Referring to FIGS. 1 through 8, the present invention may include a joint support device 10. The joint support device 10 may include a first tubular layer 24 and a second tubular layer 26. The first tubular layer 24 may include a top and a bottom. The first tubular layer 24 may be made of a plurality of crisscrossing fibers. The crisscrossing fibers may spiral from the bottom to the top. The second tubular layer 26 may also include a top and a bottom. The second tubular layer 26 may be made of a plurality of crisscrossing fibers. The crisscrossing fibers may spiral from the bottom to the top in an opposite direction that the crisscrossing fibers spiral of the first tubular layer 24. The first tubular layer 24 and the second tubular layer 26 may overlap one another.

In certain embodiments, the crisscrossing fibers of the first and second tubular layers 24, 26 may include inelastic fibers 20 and elastic fibers 18. The elastic fibers 18 may be substantially parallel with one another and the inelastic fibers 20 may be substantially parallel to one another. As illustrated in FIGS. 3 and 4, the fibers 18, 20 may start off as being perpendicular to one another. The tubular layers 24, 26 may be rotated to create the spiral, in which the elastic fibers 18 and the inelastic fibers 20 are at an acute angle relative to one another.

In certain embodiments of the present invention, the joint support device 10 may be attached to a standard elastic knee brace 12, as illustrated in FIGS. 7 and 8. The knee brace 12 may include a body portion forming an opening near the center of the body portion. The opening may allow the knee to bend. Once the first tubular layer 24 and the second tubular layer 26 are layered together, the knee brace 12 may fit within the joint support device's 10 hollow center. The edges at the top of the joint support device 10 may be sewn to the top of the knee brace 12. Likewise, the edges at the bottom of the joint support device 10 may be sewn to the bottom of the knee brace 12.

A method of making the joint support device 10 is illustrated in the Figures. The first tubular layer 24 may be suspended on a cylinder 16. The first tubular layer 24 may be twisted in a first direction, as illustrated in FIG. 4. The twisting step creates the spiral formation of the first tubular layer 24. A second tubular layer 26 may be suspended on a cylinder 16. The second tubular layer 26 may be twisted in an opposite direction of the first direction, creating a spiral directed in the opposite direction. The first and the second tubular layers 24, 26 may then be layered together to create the joint support device 10. The joint support device 10 may then be attached to the knee brace 12, as mentioned above. Once completed, the present invention may be placed on the knee of a user 14.

In certain embodiments, the first and second tubular layers 24, 26 may be rotated in multiples of three, such as about six times. In certain embodiments, a plurality of first and second tubular layers 24, 26 may be layered together so that the joint support device 10 may have a total of four, six, eight or any desired amount of layers. The joint support device 10 may be attached to the knee brace 12 with vertical sewing using binding thread 22. The present invention may function as a tension knee support for a knee size of approximately the cylinder 16. The present invention may be configured to be used with any joint such as the elbow, wrist, and ankles braces. The crisscrossing fibers of the present invention may be an elastic tubular dressing retainer by Surgilast®.

It should be understood, of course, that the foregoing relates to exemplary embodiments of the invention and that modifications may be made without departing from the spirit and scope of the invention as set forth in the following claims.

What is claimed is:

1. A method of making a joint support device comprising:
   suspending a first tubular layer on a cylinder, wherein the first tubular layer comprises inelastic fibers disposed longitudinally and elastic fibers disposed laterally;
   twisting the first tubular layer in a first direction about a longitudinal axis of the cylinder to create a first spiral;
   suspending a second tubular layer on a cylinder, wherein the second tubular layer comprises inelastic fibers disposed longitudinally and elastic fibers disposed laterally;
   twisting the second tubular layer in an opposite direction relative to the first direction about the longitudinal axis of the cylinder to create a second spiral; and
   overlapping the first tubular layer comprising the first spiral with the second tubular layer comprising the second spiral.

2. The method of claim 1, wherein the elastic fibers are substantially parallel to each other and the inelastic fibers are substantially parallel to each other prior to the step of twisting the first and second tubular layer.

3. The method of claim 1, further comprising the step of attaching a knee brace within the joint support device.

* * * * *